United States Patent
Richardson

[11] 3,958,451
[45] May 25, 1976

[54] ULTRASONIC INSPECTION APPARATUS

[75] Inventor: Anthony Charles Richardson, Houston, Tex.

[73] Assignee: Inspection Technology Development, Inc., Houston, Tex.

[22] Filed: Dec. 12, 1973

[21] Appl. No.: 426,671

[52] U.S. Cl. .............................................. 73/67.8 S
[51] Int. Cl.² .......................................... G01N 29/04
[58] Field of Search ............ 73/67.8 S, 67.8 R, 67.9, 73/71.5 US, 67, 67.5 R, 67.6, 67.7, 1 R

[56] References Cited
UNITED STATES PATENTS

| | | | |
|---|---|---|---|
| 2,532,507 | 12/1950 | Meunier | 310/8 |
| 2,953,017 | 9/1960 | Bincer et al. | 73/67.8 S |
| 3,055,210 | 9/1962 | Joy | 73/67.8 S X |
| 3,068,370 | 12/1962 | McInnish | 73/67.7 X |
| 3,121,325 | 2/1964 | Rankin et al. | 73/67.8 S X |
| 3,159,756 | 12/1964 | Beaujard et al. | 73/67.8 S X |
| 3,175,106 | 3/1965 | Sansom et al. | 73/67.8 R |
| 3,384,733 | 5/1968 | Burbank et al. | 73/67.5 R X |
| 3,575,044 | 4/1971 | Gibbs et al. | 73/67.9 |
| 3,593,569 | 7/1971 | Wilson | 73/67.7 |
| 3,688,565 | 9/1972 | Brech | 73/67.9 |
| 3,791,199 | 2/1974 | Toth et al. | 73/67.9 |
| 3,798,961 | 3/1974 | Flambard et al. | 73/71.5 US |
| 3,810,384 | 5/1974 | Evans | 73/67.8 S |

FOREIGN PATENTS OR APPLICATIONS

| | | | |
|---|---|---|---|
| 255,105 | 2/1963 | Australia | 73/71.5 US |

*Primary Examiner*—Jerry W. Myracle
*Assistant Examiner*—Stephen A. Kreitman
*Attorney, Agent, or Firm*—Vinson, Elkins, Searls, Connally & Smith

[57] ABSTRACT

An ultrasonic inspection method and apparatus for inspecting test objects such as pipeline girth welds are disclosed. Ultrasonic transducers are carried by a track circumferentially mounted around the pipeline. The transducers are mounted in a hollow, open-ended housing and a flexible seal fixed to the housing retains coupling liquid between the transducers and the pipeline to permit the propogation of waves between the transducers and the weld. An adjustable pressure regulating device maintains substantially constant liquid pressure within the housing in order to minimize the loss of coupling liquid and yet insure adequate coupling between the transducers and the weld.

2 Claims, 21 Drawing Figures

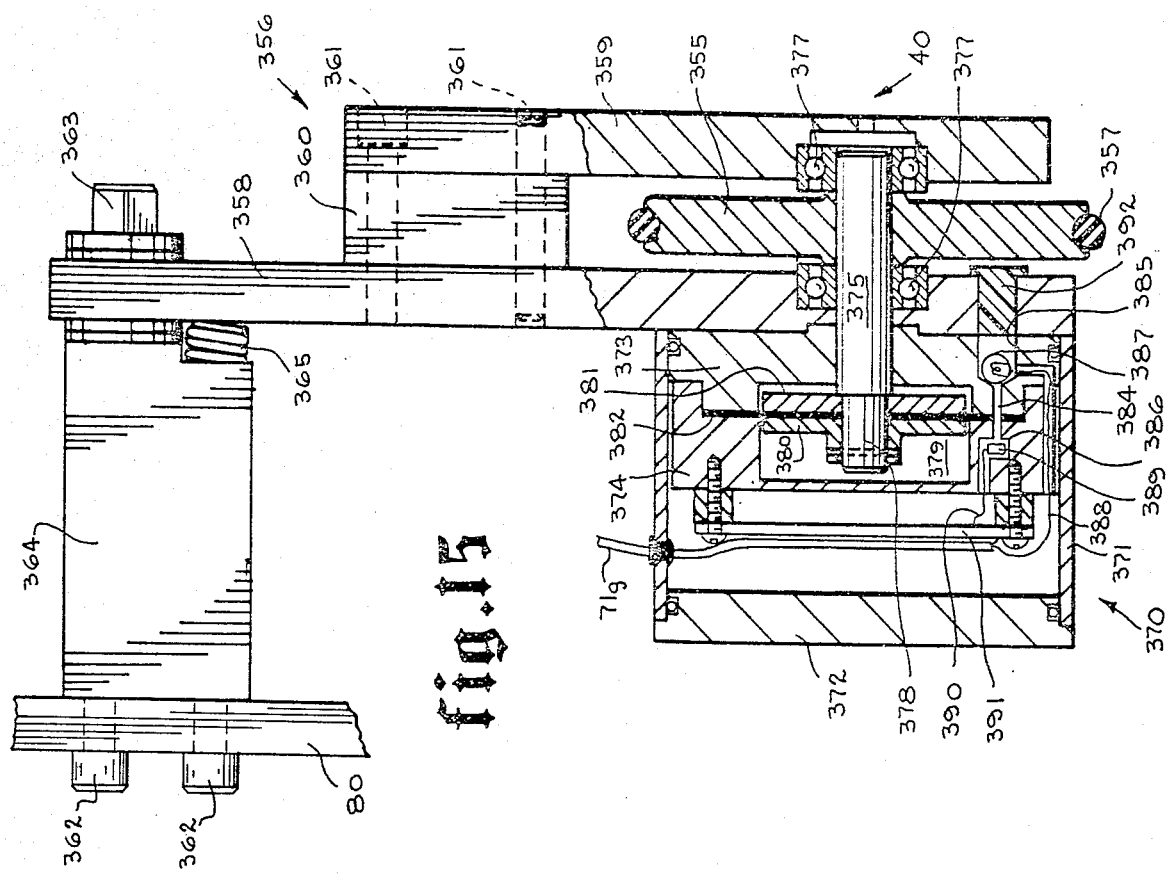

ULTRASONIC INSPECTION APPARATUS

BACKGROUND OF THE INVENTION

1. Field

This invention relates to the automatic ultrasonic inspection of welds and other test objects. The invention particularly relates to the automatic inspection of the circumferential welds which join together sections of pipelines which transmit petroleum products and other fluids. These welds are known as girth welds. Recently automatic devices have been developed for rapidly welding together sections of pipeline. These automatic devices typically carry a welding device around the pipeline on a tack which is mounted circumferentially on the pipeline. These devices occasionally malfunction and reproduce the same type of flaw in weld after weld. For this reason it is important quickly to detect the presence of an unacceptable flaw in such a weld and to correct the malfunction before additional defective welds are produced. Detecting flawed welds before the pipeline is buried is important because unearthing buried pipeline is very expensive and because a pipeline explosion can destroy property and take human lives.

2. Prior Art

Inspecting welds and other test objects by devices which move along the welds, transmit ultrasonic waves into the welds and detect ultrasonic waves reflected back from the welds is not new. See, for example, U.S. Pat. No. 2,953,017 (1960) to Bincer, et al., U.S. Pat. No. 3,068,370 (1962) to McInnish, U.S. Pat. No. 3,213,676 (1965) to Makous, U.S. Pat. No. 3,248,933 (1966) to Stebbins, U.S. Pat. No. 3,575,044 (1971) to Gibbs and U.S. Pat. No. 3,712,119 (1973) to Cross. As used in this description and in the claims, the term "weld" includes not only the filler, or the metal added, but also the adjacent heat-affected zones of the metal joined by the filler. As used herein, the term "reinforcement" of a weld shall mean the cap on the external surface of the weld or the stringer bead on the internal surface of the weld. Typically these reinforcements are convex accumulations of metal at the upper and lower boundaries of the weld and reflect ultrasonic waves.

The ultrasonic transducers used in such devices are well known in the art and throughout this description and in the claims will be referred to as "ultrasonic transducers" or simply "transducers". These transducers have crystals which are electrically energized and which transmit ultrasonic waves into adjacent regions. Conversely, the crystals may receive ultrasonic waves impinging on the crystals and the transducers may convert these received waves by well known means into electrical signals for display on oscilloscope screens or other media. As used throughout this description and in the claims, these ultrasonic sound waves will be referred to as "ultrasonic waves" or simply "waves".

In the prior art, automatic ultrasonic devices for inspecting girth welds may include a track placed around the pipeline near the weld. The transducers may be carried in an open-ended housing which is mounted on a carriage guided by the track and is carried along the track adjacent the weld to inspect the weld. See, for example, U.S. Pat. No. 3,248,933 to Stebbins. Coupling liquid such as water may be interposed between the transducers and the pipeline to improve the propagation of ultrasonic waves between the transducers and the pipeline. This liquid may be retained around the transducers by a flexible seal or gasket which is mounted around the open end of the housing and which slidably engages the pipeline.

A problem unsolved in the prior art is the problem of rapidly and properly aligning the path of the transducers with respect to the weld, so that the transducers will traverse the weld with distances from the weld and angular orientations or attitudes with respect to the weld maintained substantially constant. Undesired changes in such distances and angular orientations can render the signals received from the transducers meaningless and can necessitate the continuous and time consuming reorientation and recalibration of the inspection apparatus.

In the known prior art, no satisfactory technique has been developed for keeping the loss of coupling liquid minimal and yet insuring that there is always coupling liquid between the transducers and the pipeline. Inevitably, some liquid will leak, particularly if the surface of the pipeline is rough. If this leakage becomes too great, air may intrude between the transducers and the pipeline and the propagation of ultrasonic waves will be greatly diminished or interrupted, with resulting confusion in the meaning of the signals from the transducers. The likelihood of such an interruption may be decreased by increasing the pressure of the water in the apparatus, but this step increases the amount of liquid cost during the inspection of each weld. In many kinds of terrain, great loss of such liquid, even if only water, is unacceptable.

In the known prior art, no satisfactory method has been devised for correlating accurately the indications of flaws in the weld with the position of the transducers at the time such flaws were detected in order to determine the location of the flaws. This correlation is particularly important when the transducers are traversing rapidly a lengthy weld.

When a wave transmitted from one of the transducers reaches the top or the bottom reinforcement of a weld, at least part of that wave will be reflected by the reinforcement. It is important to distinguish such reflected waves from those other waves reflected by actual flaws in the weld. In the known prior art, no satisfactory method is shown for eliminating signals associated with waves reflected by the upper and lower boundaries of the welds and received by the transducers.

SUMMARY

Applicant solves the problem of rapidly and properly aligning the path of the transducers with respect to the weld by carrying the transducers on a track and carriage similar in design to the track and carriage used to carry the welding device which formed the weld under inspection. When possible, as when a new pipeline is being constructed, the transducers are carried by the same track which carried the welding device before that track is moved from the position in which it carried the welding device. This method clearly greatly facilitates the proper alignment of the transducers as they traverse the weld.

Applicant solves the problem of keeping the loss of coupling liquid minimal and yet insuring that there is continually coupling liquid between the transducers and the pipeline during the test or inspection by providing a pressure regulating device which maintains the liquid pressure within the housing substantially constant. This pressure may be preselected according to the particular welds and pipeline being inspected to minimize the loss of coupling liquid.

Applicant solves the problem of determining the location of detected flaws by providing an odometer mounted on the apparatus near the transducers. The wheel of this odometer engages the outer surface of the pipeline and the revolutions of the odometer as the transducers traverse the surface of the pipeline give an accurate measure of the distance traveled by the transducers from a known starting point.

Applicant solves the problem of eliminating signals associated with waves reflected by the upper and lower reinforcements of the welds by setting electronic gates to eliminate such signals. The gates are set by means of gate calibration blocks which have notches with surfaces which reflect ultrasonic waves. Before testing, the notches are positioned with respect to the transducers so that the surfaces of the notches are at the far boundaries of the regions to be tested by the respective transducers. The electronic gates are set to exclude all signals caused by waves reflected from any region of the weld beyond those boundaries. Thus, when the weld is tested, spurious signals such as those caused by waves reflected from the reinforcements of the weld, are excluded.

Thus, an object of this invention is rapidly and properly to align the path of the transducers as they traverse the weld by using a track and carriage similar in design to the track and carriage which carried the welding device which formed the weld. When possible, the transducers are carried by the same track which carried the welding device and are mounted on that track before it is moved after the welding operation.

Another object of this invention is to provide an ultrasonic inspection apparatus which continually maintains coupling liquid between the transducers and the test object, yet which loses only a minimal amount of coupling liquid.

Another object of this invention is to determine the location of detected flaws by providing an odometer mounted on the apparatus to provide an accurate indication of the distance traveled by the transducers along the surface of the test object from a known point.

Another object of this invention is to set electronic gates to eliminate signals not indicative of flaws by positioning reflective surfaces before testing at the boundaries of the regions to be tested in order to provide reference points for setting the gates.

Other objects will be apparent from the drawings, the specification and the claims.

BRIEF DESCRIPTION OF THE DRAWINGS

In the drawings wherein like reference numerals indicate like parts and wherein the illustrative embodiments of this invention are shown:

FIG. 13 is a side view partly in elevation and partly in section of the pressure regulating device of the inspection apparatus, showing the pressure regulating device in condition for permitting the flow of coupling liquid to the transducer mounting block;

FIG. 14 is a side view partly in elevation and partly in section of the pressure regulating device, showing said device in condition for preventing the flow of coupling liquid to the transducer mounting block;

FIG. 15 is a top view partly in elevation and partly in section of the odometer which measures the distance of travel of the transducers around the pipeline;

DESCRIPTION OF THE PREFERRED EMBODIMENTS

The ultrasonic inspection apparatus which embodies this invention may be considered to include two basic sections. The first basic section causes the transducers and certain other components of the ultrasonic inspection apparatus to traverse the surface of the test object. This first basic section thus may be referred to broadly as "means for moving" the transducers and other components of the inspection apparatus. In the preferred embodiment, this first basic section includes a track mounted circumferentially around the pipeline and a carriage which is carried by the track. Such a track and carriage in themselves are old, but are combined in novel ways with other components of the apparatus. The second basic section of the ultrasonic inspection apparatus is an inspection subsystem which will be described in detail below. Some components of this subsystem such as the odometer and the test head which contains the transducers, are mounted on the carriage and are carried around the pipeline by the track and carriage. For ease of expression, these components which are mounted on the carriage may be referred to herein as the "carriage-mounted components". Other components of the inspection subsystem, such as the light beam recorder, are not carried by the track and carriage, but are connected to the carriage-mounted components as now will be described.

Figure 1:
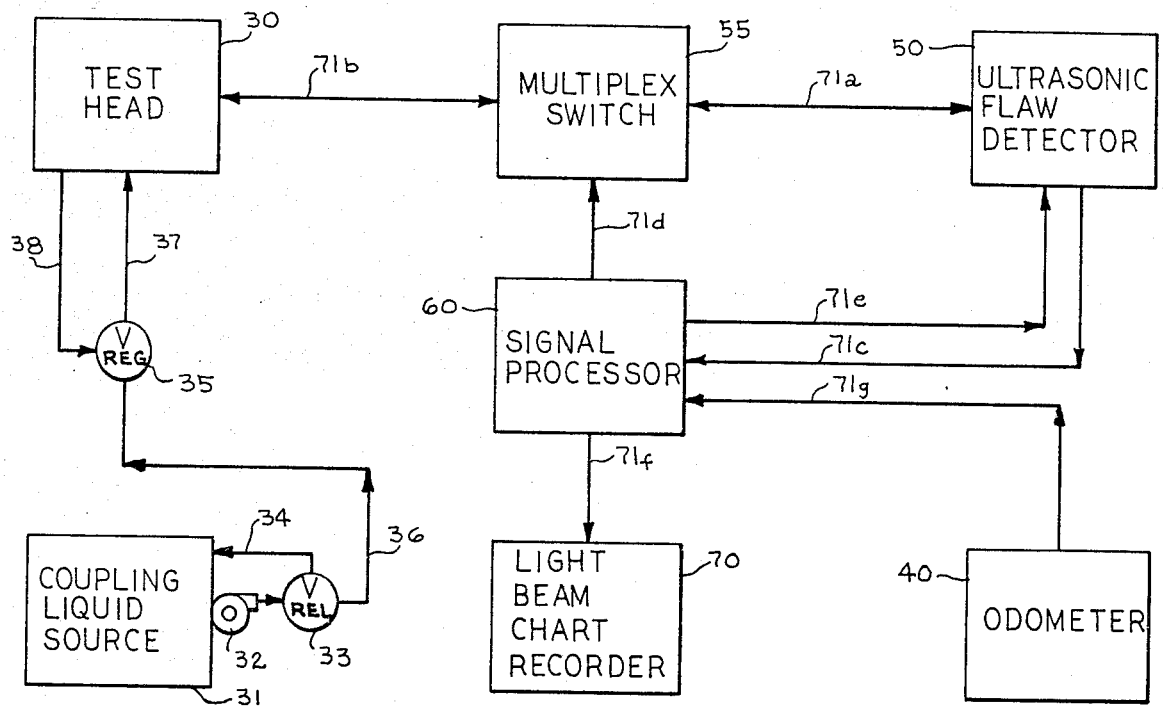
FIG. 1 is a schematic illustration of the major components of the inspection subsystem of an apparatus embodying the invention and shows the relationships between those components.

FIG. 1 illustrates the conceptual relationship of the major components of the inspection subsystem of the apparatus. The test head 30 includes the ultrasonic transducers which circumferentially traverse the surface of the pipeline, transmit ultrasonic waves into the pipeline and receive ultrasonic waves reflected from the pipeline. As used herein, "test object" means any object, such as a pipeline, including the welds of a pipeline, which is tested by this inspection apparatus. As will be apparent, this invention is by no means limited to testing girth welds, or pipelines, or even tubular goods, but may be used for testing many differently shaped test objects.

Ultrasonic transducers are old in the art and can be bought from many public sources. They may be designed only to generate ultrasonic waves, or only to receive ultrasonic waves, or both to generate and receive ultrasonic waves. In the preferred embodiment, ultrasonic transducers which both emit and receive ultrasonic waves are used. However, it is readily apparent that the use of such transducers is by no means necessary for the practice of the invention. In the preferred embodiment, ¼ inch diameter, five megahertz transducers and ½ inch diameter, 5 megahertz transducers are used. Both may be purchased from Aerotech Laboratories in Lewistown, Pennsylvania. These transducers may be referred to as transmitting and sensing means for transmitting ultrasonic waves into the test object and for detecting ultrasonic waves reflected from flaws in the test object. Clearly transducers of other diameters or frequencies may be used without departing from the scope of the invention.

The test head 30 communicates with a coupling liquid source 31. Coupling liquid from source 31 is maintained in the test head 30 between the pipeline and transducers and permits the propagation of ultrasonic waves between the pipeline and the transducers. A pump 32 pumps coupling liquid from the source 31 to the test head 30. A pressure relief valve 33 of a character well known in the art returns liquid to the source 31 via conduit 34 when required to maintain constant pressure to conduit 36. As will be explained in detail below, a pressure regulating device 35 maintains the coupling liquid in the test head at a constant preselected pressure. Said coupling liquid flows from valve 33 via conduit 36. When the pressure of the coupling liquid in the test head 30 is below a preselected level, the pressure regulating device 35 permits the coupling liquid to flow through device 35 and conduit 37 to the test head 30. However, the conduit 38 communicates between the test head 30 and the pressure regulating device 35 and carries coupling liquid from said test head 30 to said device 35. When the pressure of the coupling liquid in said head 30 reaches said preselected level, coupling liquid flowing through said conduit 38 from the test head 30 to the device 35 causes the device 35 to shut off the flow of coupling liquid through device 35 and conduit 37 to the test head 30.

The odometer 40 travels around the pipeline with the test head 30 and measures the distance traveled by the test head 30 from a fixed point.

The ultrasonic flaw detector 50 is a standard off-the-shelf instrument well known to those skilled in the art. Basically, this flaw detector is an oscilloscope suitable for ultrasonic pulse-echo applications. Such flaw detectors may be purchased from many sources. In the preferred embodiment, a Branson Model S5 flaw detector purchased from Branson Instruments Company, Stamford, Conn. is used. This ultrasonic flaw detector 50 generates excitation pulses which are transmitted to the transducers in the test head 30 through multiplex switch 55 and which cause those transducers to transmit ultrasonic waves through the coupling liquid into the pipeline. Cable 71a connects ultrasonic flaw detector 50 and multiplex switch 55; cable 71b connects multiplex switch 55 and test head 30. The ultrasonic flaw detector 50 also receives from the transducers via cables 71a and 71b signals caused by and corresponding to ultrasonic waves reflected back from the pipeline through the coupling liquid and received by the transducers. In addition, the flaw detector 50 displays on its screen said signals received from the transducers and transmits via cable 71c said signals to the signal processor 60. Thus, the screen of the flaw detector 50, which is an oscilloscope screen, may be called means for monitoring the ultrasonic waves reflected from flaws and detected by the transducers. However, clearly the waves and the signals which they cause may be monitored by means other than the screen, such as the chart recorder described below.

Multiplex switch 55 is controlled by the signal processor 60 and sequentially directs signals between the flaw detector 50 and the transducers in test head 30. In the preferred embodiment, the test head 30 contains four transducers, each of which transmits and receives ultrasonic waves. To avoid interference and spurious signals, these transducers are activated sequentially. The signal processor 60 controls the sequential activation of the transducers by periodically transmitting signals to the multiplex switch 55 via cable 71d. At a first point in time, multiplex switch 55 permits the transmission of signals between flaw detector 50 and a given first transducer, but not between flaw detector 50 and any other transducer. When multiplex switch 55 receives a signal from the signal processor 60, it terminates the transmission between that first transducer and flaw detector 50 and permits transmission between flaw detector 50 and a second transducer. The signal processor 60 then sends a signal to flaw detector 50 via cable 71e causing flaw detector 50 to send an excitation pulse to said second transducer through cable 71a, the multiplex switch 55 and cable 71b. That second transducer then generates an ultrasonic wave which propagates through the coupling liquid and into the pipeline to the weld; a flaw in the weld or other discontinuity in the pipeline will cause a wave to be reflected back to that transducer which will then transmit corresponding signals to the flaw detector 50. The flaw detector 50, as explained above, amplifies these signals, displays them on the screen and transmits them to the signal processor 60. As will be explained in detail below, the signal processor 60 then gates the received signals to eliminate irrelevant portions of the signals and retain only those portions indicative of an actual flaw in the weld. The gated flaw signals are then transmitted via cable 71f to the light beam chart recorder 70 for recordation on a strip chart. The signal processor 60 then sends a signal to multiplex switch 55 via cable 71d. This signal causes the multiplex switch 55 to stop transmission between the second transducer and flaw detector 50 and to establish transmission between flaw detector 50 and a third transducer only, in order to activate the third transducer. This sequential operation is continued for as long as the weld is being tested. The signal processor 60 also receives signals from the odometer 40 via cable 71g and transmits those signals to the chart recorder 70 via cable 71f for recordation on the strip chart.

The light beam chart recorder 70 is a standard recorder which may be purchased from numerous sources. The recorder 70 receives signals from the signal processor 60 and makes a permanent visual record of those signals for interpretation. In the preferred embodiment, a Rapet RMS 11 recorder from Kyowa Electronic Instruments Co. Ltd., Tokyo, Japan is used. This recorder makes on a strip chart a separate trace of the signals from each of the four transducers and also records next to said traces a trace from the odometer indicating the distance traveled by the test head around the pipeline. Thus, the recorder may be referred to as recording means for recording signals from the odometer and from flaws in the pipeline or other test object.

A power supply (not shown) transmits power to the flaw detector 50, signal processor 60, the chart recorder 70 and other components of the apparatus. This power supply may be any acceptable source of electric current, such as batteries, a portable generator, or utility company generators, all well known in the art.

Figure 3:
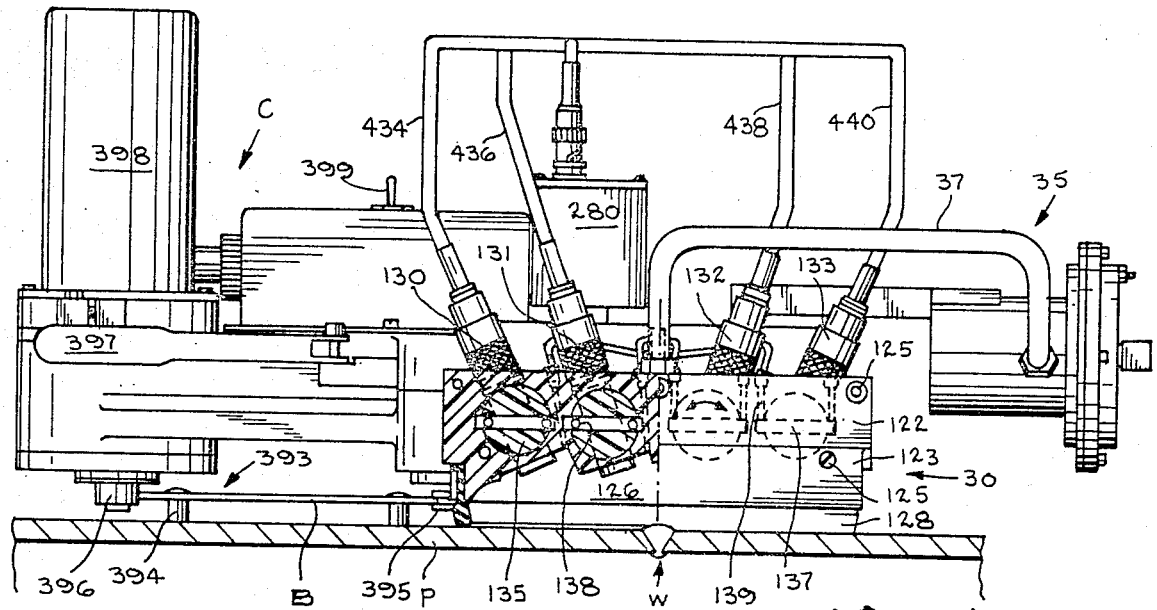
FIG. 3 is a view partly in section and partly in front elevation taken along line 3—3 in FIG. 2.
Figure 2:
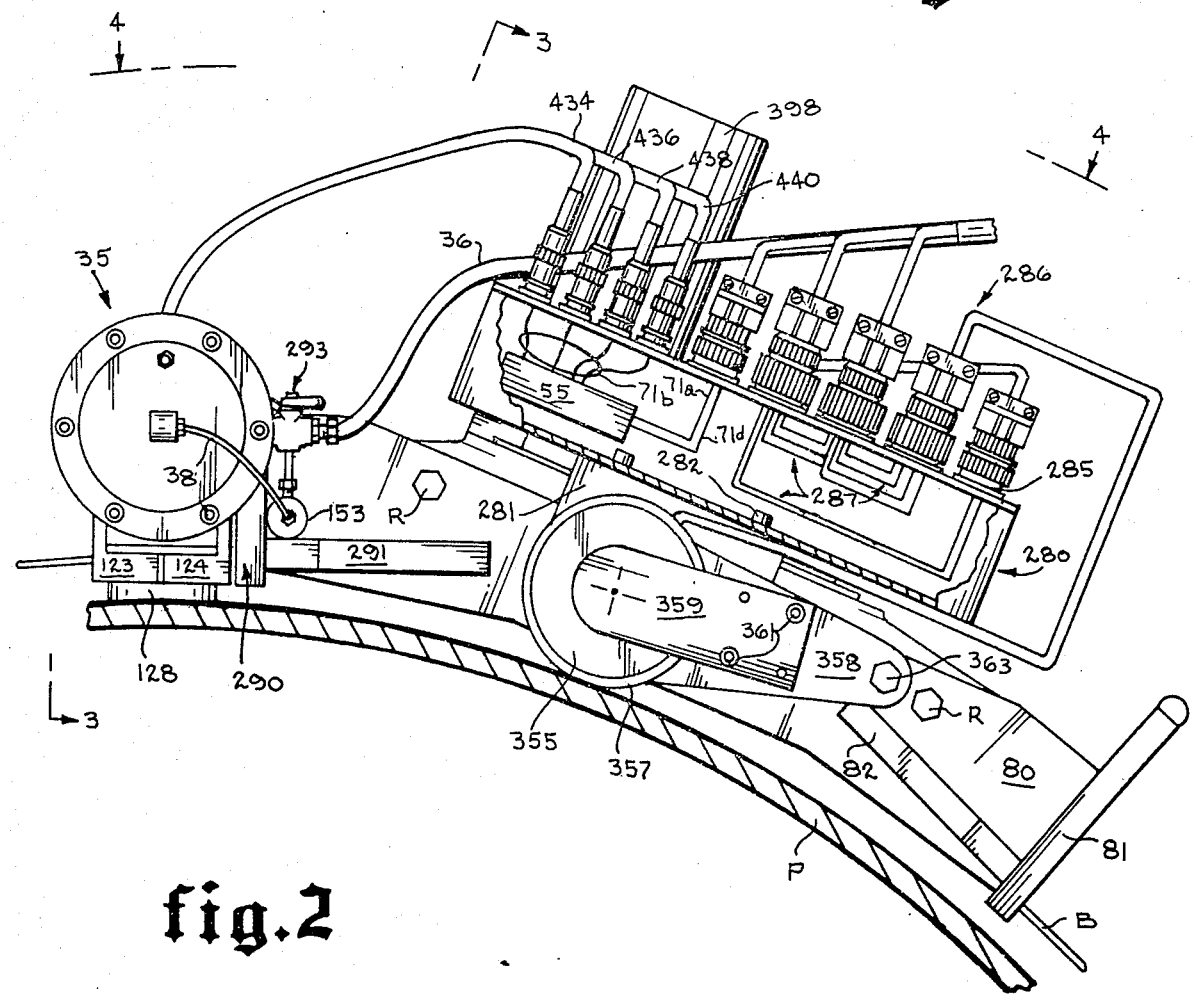
FIG. 2 is a view partly in section and partly in side elevation of certain components of an inspection apparatus embodying the invention and in place on a pipeline.
Figure 4:
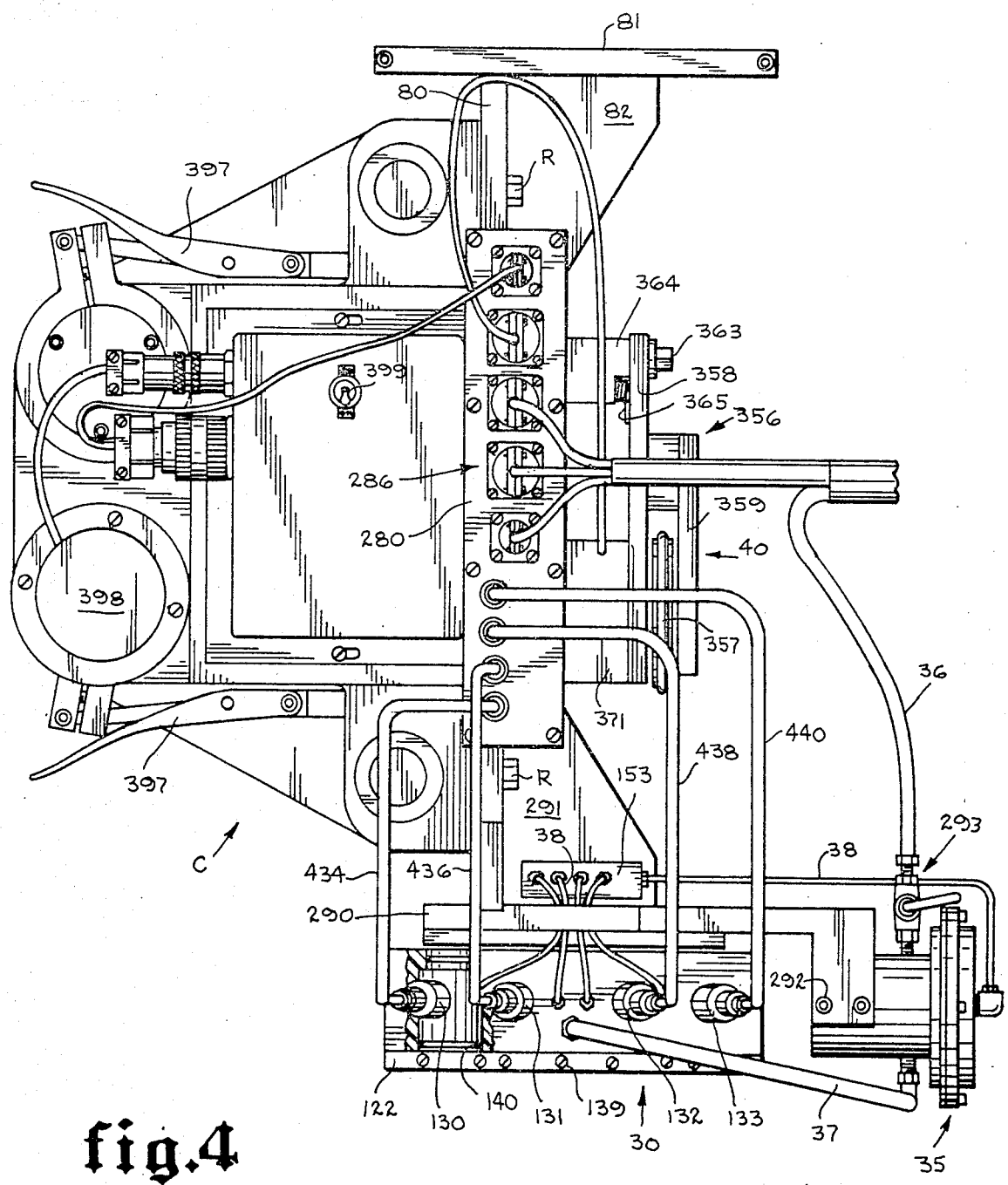
FIG. 4 is a view partly in section and partly in top elevation and taken along line 4—4 in FIG. 2.

FIGS. 2, 3 and 4 show the various components of inspection apparatus in position to inspect pipeline P. The apparatus comprises a side frame plate 80 on which are mounted the test head 30, the pressure relief device 35, the odometer 40 and the multiplex switch 55.

The inspection apparatus moves around the pipeline P clockwise as seen in FIG. 2. For the purpose of protecting the rest of the apparatus and moving obstacles from the path of the apparatus, a front plate 81 is mounted to the forward end of frame plate 80 and is supported by gusset 82.

Figure 5:
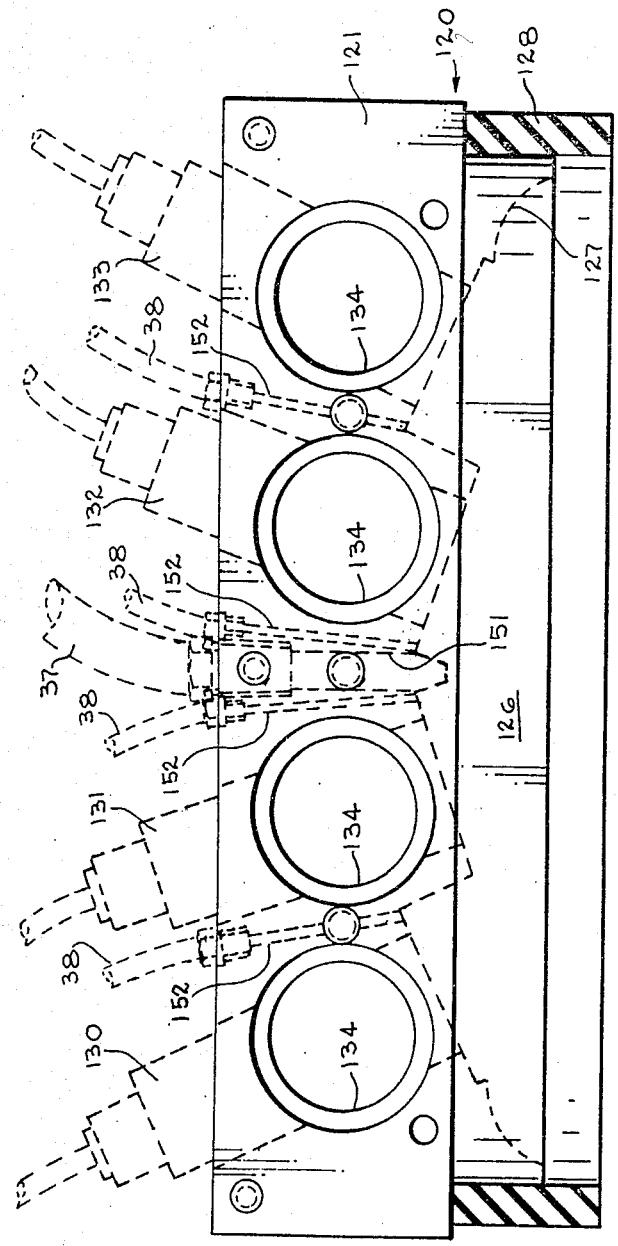
FIG. 5 is a view partly in section and partly in side elevation of the transducer mounting block of the inspection apparatus, with the cover plate and seal clamps removed therefrom.
Figure 6:
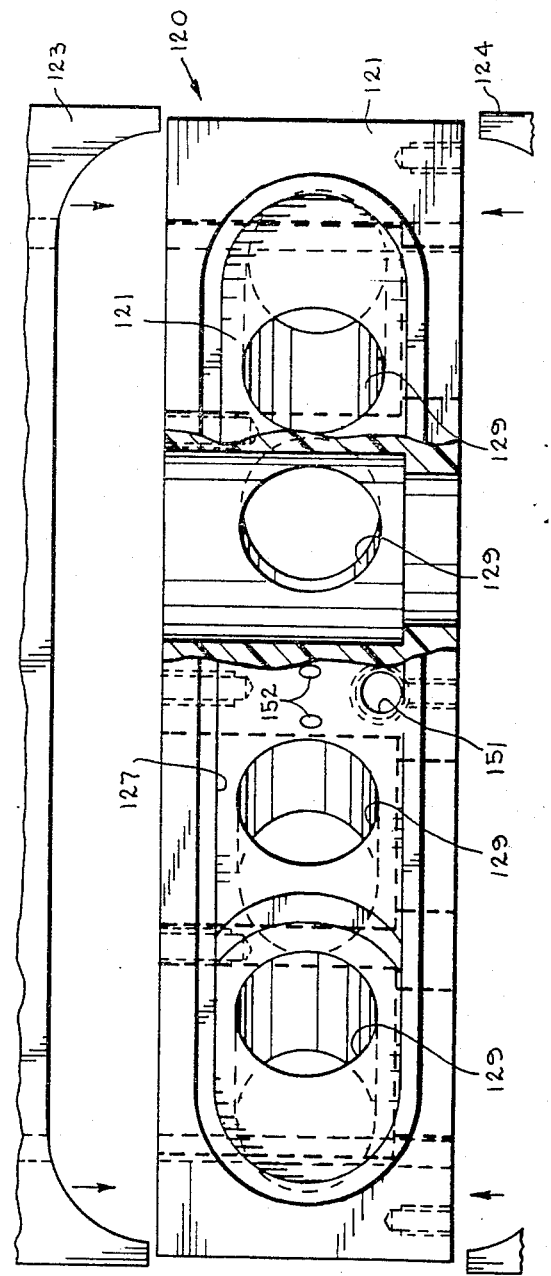
FIG. 6 is a view partly in section and partly in elevation of the under side of the transducer mounting block, with the seal clamps in exploded position.

The test head, which is indicated generally at 30, includes a generally box-shaped housing 120 which is illustrated in detail in FIGS. 5 and 6. For ease of construction, housing 120 comprises a plastic transducer mounting block 121, an aluminum cover plate 122, and aluminum seal clamps 123 and 124, all joined together by suitable means such as screws 125. However, clearly the housing 120 could be formed from one piece of material other than aluminum or plastic. The lower edges of the mounting block 121 and clamps 123 and 124 define a hollow chamber 126 with an oval-shaped opening 127 toward the pipeline P. A resilient seal or gasket 128 is attached around the edge of the oval-shaped opening 127. This seal 128 slidably engages the pipeline P and retains coupling liquid in the hollow chamber 126 as the housing 120 traverses the surface of the pipeline to inspect weld W, as will be explained below.

Four transducers bores 129 extend from hollow chamber 126 upwardly through mounting block 121 to the exterior of block 121. Four transducers 130, 131, 132 and 133 are disposed in these bores 129. In order to permit slight angular adjustments of the transducers in bores 129, the diameters of bores 129 are slightly larger than the diameters of the transducers which they receive. In the preferred embodiment, transducers 130 and 133 are the ½ inch diameter transducers and transducers 131 and 132 are the ¼ inch transducers, but obviously many sizes of transducers can be used without departing from the scope of the invention. As may be seen best in FIG. 6, these bores 129 preferably lie along a line parallel to the longitudinal axis of mounting block 121, so that when the weld is inspected, the transducers 130-133 lie along a line perpendicular to the path of travel of the transducers. Further, as shown in FIG. 3, the bores 129 are canted so that the transducers point generally toward weld W.

Figure 21:
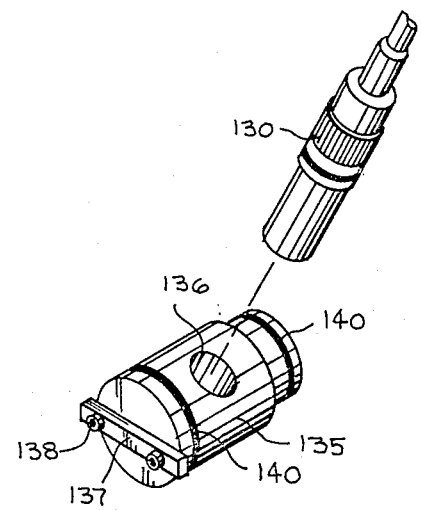
FIG. 21 is an exploded view in perspective of a plug which holds a transducer and fits into the transducer mounting block.

Four horizontal holes 134 are formed in mounting block 121 and each hole 134 intersects a different transducer bore 129. In order to hold transducers 130-133 in bores 129, four cylindrical plugs 135 are provided. These plugs fill holes 134 and have passageways 136 which receives the transducers as illustrated in FIG. 21. An arm 137 is fastened to the outer end of each plug by screws 138. When plugs 135 and transducers 130-133 are in place in the mounting block 121, as in FIG. 3, the plugs 135 fill holes 134 and hold the transducers in place in bores 129. Screws 139, extending through holes in cover plate 122 bear on the ends of arms 137. The adjustment of screws 139 causes plugs 135 to rotate within small limits about their longitudinal axes and thus changes the attitudes of the transducers 130-133 within small limits as desired. In order to prevent coupling liquid from leaking through holes 134, O-rings 140 are mounted circumferentially around each end of the plugs 135.

For the purpose of introducing coupling liquid into chamber 126, a vertical entrance port 151 extends through the top of said mounting block 121 from the exterior of said block to the chamber 126. As seen best in FIG. 5, the conduit or hose 37 is connected to said entrance port 151 so that coupling liquid can flow from the pressure regulating device 35 through conduit 37 and port 151 to chamber 126.

For the purpose of expelling air and coupling fluid from chamber 126, four generally vertical exit ports 152 extend from the chamber 126 to the exterior of mounting block 121. As seen best in FIG. 4, these exit ports 152 are joined with the ends of conduits or hoses 38. The hoses 38 extend to a manifold 153, where their flow is united, and from there to the pressure regulating device 35 via conduit 38.

The coupling liquid may be any liquid, such as water, suitable under the conditions of use for improving or making possible the propagation of ultrasonic waves between the transducers 130-133 and the pipeline P. In freezing weather, antifreeze may be desirable.

Figure 7:
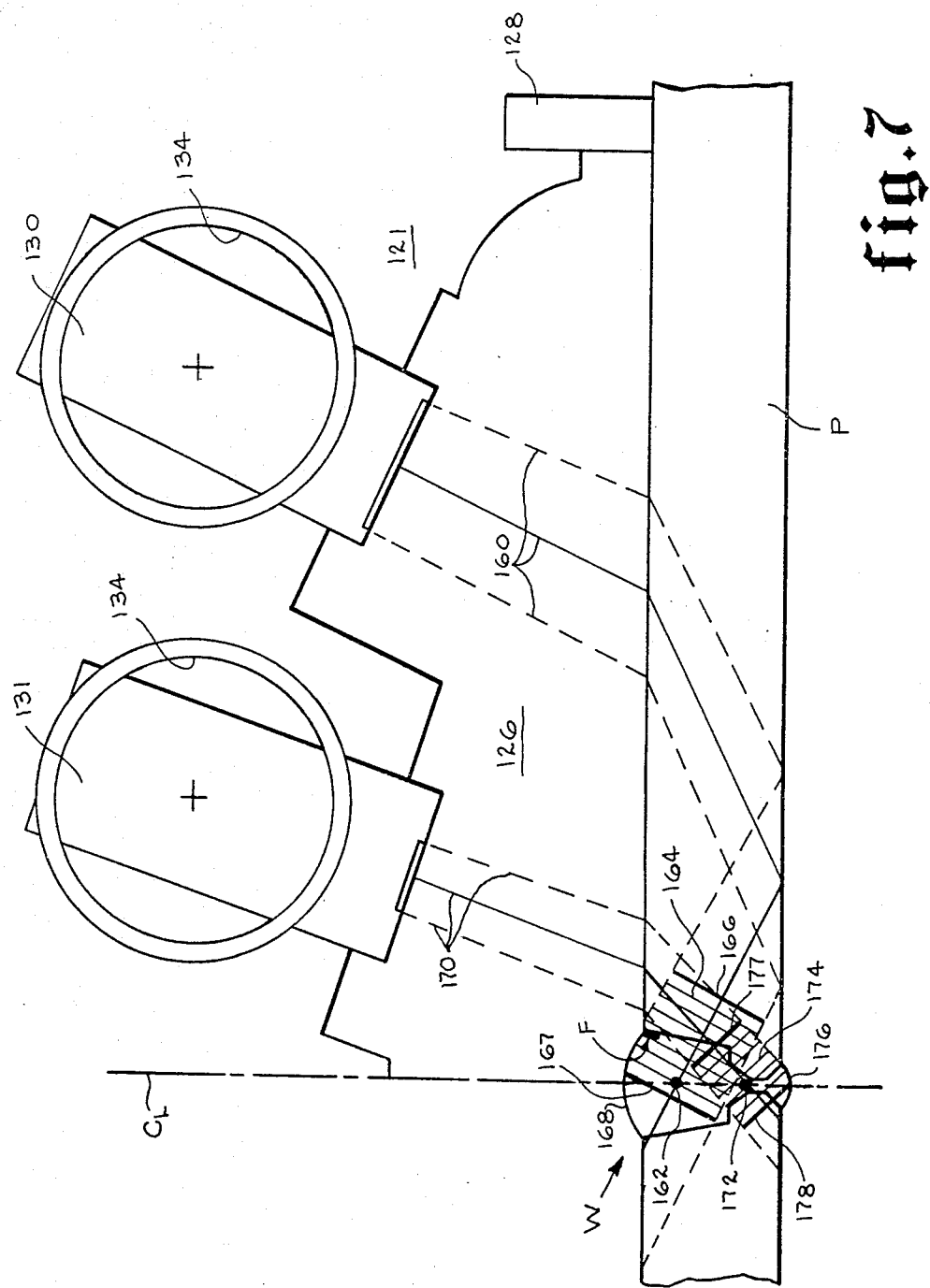
FIG. 7 is a schematic illustration of the propagation of ultrasonic waves between the weld and the transducers.

The propagation of ultrasonic waves between the transducers 130 and 131 and the pipeline P is illustrated schematically in FIG. 7. For the purpose of the description and the claims herein, waves traveling through different media are discussed as if they are continuous waves even though the waves in the liquid are believed to be longitudinal while those in the pipeline are believed to be transverse. Transducers 130 first emits an ultrasonic wave 160 illustrated by lines 160. This wave propagates through the liquid-filled chamber 126, is refracted and mode converted when it enters the pipeline P, is reflected from the interior surface of pipeline P and propagates through the weld W. As is apparent from FIG. 7, this wave 160 is centered on imaginary point 162 when it passes through the vertical center line CL of weld W. To eliminate spurious signals not indicative to flaws, the region 164 desired to be inspected by this wave 160 is a relatively small region and is designated with a group of lines slanting downwardly to the left. For ease of expression, a region desired to be inspected may be referred to herein as a region of interest. As may be seen in FIG. 7, the near boundary of region of interest 164 is represented by imaginary line 166 and the far boundary of region 164 by imaginary line 167. The wave 160 impinges on flaw F and an echo wave returns along the path of wave 160 and is received by transducer 130 which transmits a corresponding signal to the flaw detector 50. A similar echo wave is reflected from a surface of the cap or reinforcement 168 of weld W. This surface of cap 168 lies outside of region 164.

Then transducer 131 emits an ultrasonic wave 170 illustrated by lines 170. This wave propagates through the coupling liquid in chamber 126, is refracted when it enters pipeline P and passes through part of weld W. When wave 170 passes through the center line CL of weld W, it is centered on imaginary point 172. Also to eliminate spurious signals not indicative of flaws, the region 174 desired to be inspected by wave 170 and thus transducer 131 is relatively small. In particular, region 174, indicated by a group of lines slanting downwardly to the right, does not include that surface of the stringer bead or reinforcement 176 which will reflect echos back to transducer 131. The near boundary of region 174 is indicated by imaginary line 177 and the far boundary by imaginary line 178.

Regions of interest 164 and 174 thus have been defined to include parts of the weld W, but to exclude those surfaces of reinforcements 168 and 176 which reflect waves not indicative of flaws to transducers 130 and 131. Transducers 132 and 133 of course are disposed in housing 120 symmetrically to transducers 131 and 130 respectively about center line CL. These transducers 132 and 133 have regions of interest which are symmetrical about center line CL to regions 174 and 164 respectively and which, like regions 174 and 164, exclude those surfaces of the reinforcements which reflect waves not indicative of flaws to transducers 132 and 133. Thus, collectively the four regions of interest of the four transducers include the entire weld W and do not include reflective surfaces of the reinforcements 168 and 176 which will reflect spurious signals to the transducers.

Figure 17:
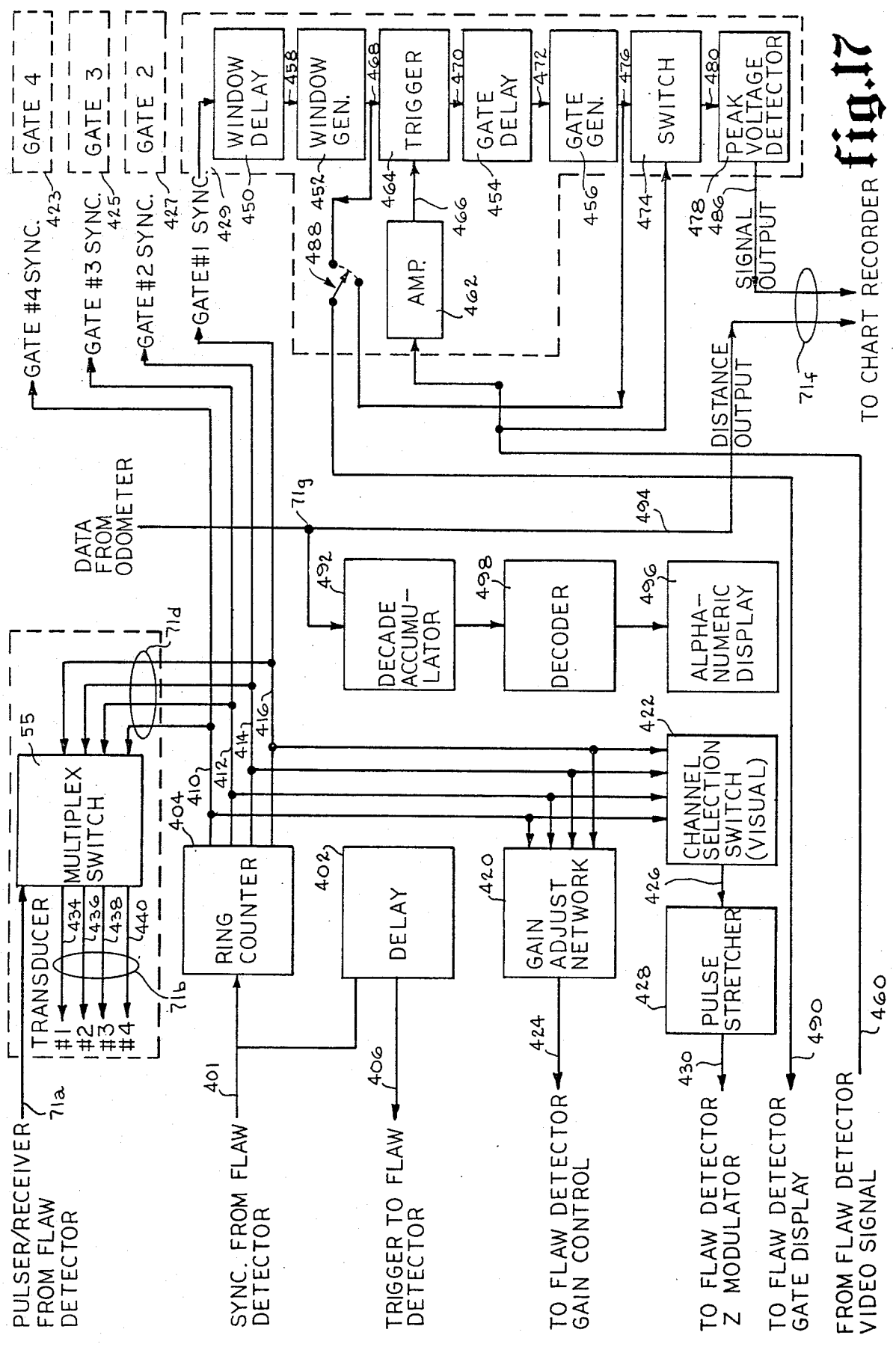
FIG. 17 is a schematic illustration of the electronic circuitry associated with the signal processor and the multiplex switch.

In order to facilitate the analysis of waves which are reflected and then received by transducers 130–133, before inspection of the weld, the angular orientation or attitudes of the transducers are adjusted or calibrated so that the waves from transducers 130 and 133 are centered on point 162 when they propagate through center line CL of weld W and so that the waves from transducers 131 and 132 are centered on point 172 when they propagate through center line CL. This calibration is accomplished by means of a transducer calibration block. Further, a gating network is provided to eliminate signals corresponding to waves reflected from parts of the weld other than the regions of interest of the transducers 130–133. This gating network is part of the signal processor 60 and its electronics are illustrated in FIG. 17 and described below. Before the weld is inspected, the gating network is adjusted or calibrated to eliminate or exclude undesired signals. An electronic gate is associated with each transducer to eliminate or exlude signals corresponding to waves received by that transducer from areas other than that transducer's region of interest. First, the gate is calibrated to exclude signals corresponding to waves from beyond the far boundary of that transducer's area of interest. This far boundary calibration is accomplished by means of gate calibration blocks. Then, as will be explained in connection with FIG. 17, the gate is calibrated by time reference to the far boundary to exclude signals from waves reflected from areas before the near boundary.

The calibration blocks are illustrated in FIGS. 8 through 12. The transducers and gates are calibrated by positioning the calibration blocks one at a time next to seal 128, filling chamber 126 with coupling liquid and transmitting waves from the transducers into the calibration blocks. Preferably these blocks are of the same thickness and material as the pipeline to be tested, so that waves in them will propagate similarly to waves in the pipeline. These blocks are machined, as will be discussed in detail, to provide reflective discontinuities at positions corresponding to points 162 and 172 and far boundary lines 167 and 178 in FIG. 7 and the far boundary lines of the regions of interest of transducers 132 and 133.

Figure 8:
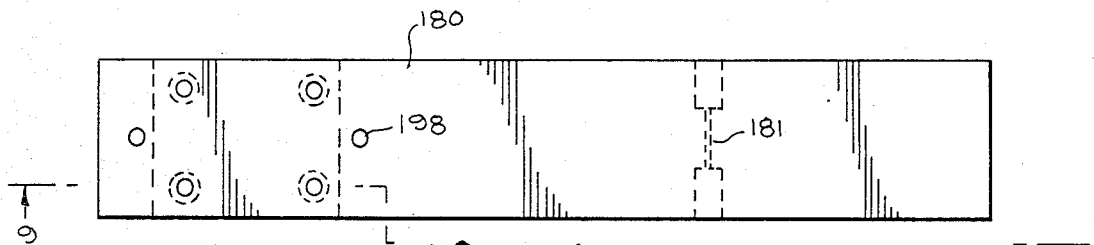
FIG. 8 is a top elevational view of a transducer calibration block used in adjusting the angular orientations of the transducers before testing.
Figure 9:
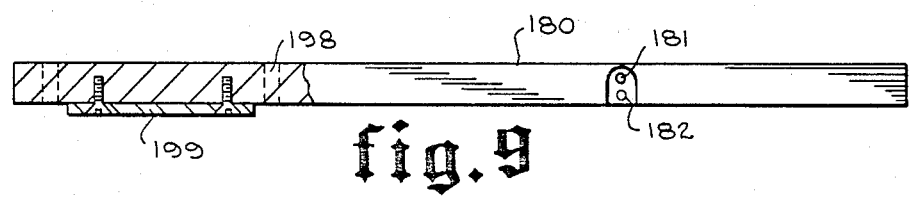
FIG. 9 is a view partly in elevation and partly in section taken along line 9—9 in FIG. 8.

Transducers calibration block 180 in FIGS. 8 and 9 is for calibrating the angular orientations or attitudes of the transducers before the inspection in order to center the waves from the transducers on imaginary points 162 and 172 when the waves propagate through the weld W. Block 180 has two holes 181 and 182 which reflect ultrasonic waves and which are spaced apart the same distance as the distance separating points 162 and 172 in FIG. 7. These holes 181 and 182 are centered under the transducers so that they bear the same spatial relationship to the transducers as do points 162 and 172 in FIG. 7 when the weld is inspected or tested. The angular orientations of the transducers 130–133 in mounting block 121 are then adjusted by turning screws 139 to maximize the signals from waves reflected from holes 181 and 182. In this way, the transducers 130 and 131 are oriented to direct the waves into the desired regions of the weld W when the weld is tested.

Figure 10:
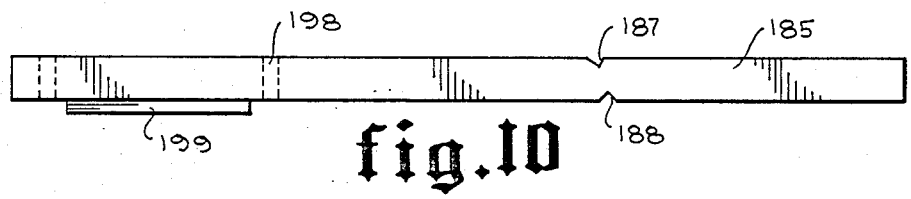
FIG. 10 is a side elevational view of a gate calibration block used in setting the electronic gates before testing.
Figure 11:
FIG. 11 is a side elevational view of another gate calibration block.

Gate calibration blocks 185 and 186 in FIGS. 10 and 11 are for calibrating the electronic gates to exclude signals from waves reflected from regions of the weld beyond the far boundaries of the regions to be tested. Block 185 has two notches with surfaces 187 and 188 which bear the same spatial relationship as far boundary lines 167 and 178 in FIG. 7. These surfaces reflect ultrasonic waves. As with block 180, before inspection block 185 is placed under seal 128 so that surfaces 187 and 188 are at the far boundaries of the regions to be tested by transducers 130 and 131. As will be explained in detail below, the electronic gates for each transducer 130 and 131 are set to exclude signals caused by waves reflected from any region beyond said surfaces 187 and 188. In this way, the gates are set to exclude during the inspection of weld W any signals caused by waves reflected from any region beyond far boundaries 167 and 178.

In a like manner, block 186 is machined with notches having reflective surfaces 189 and 190 suitable for setting the gates which define the far boundaries of the regions of interest for transducers 132 and 133.

Figure 12:
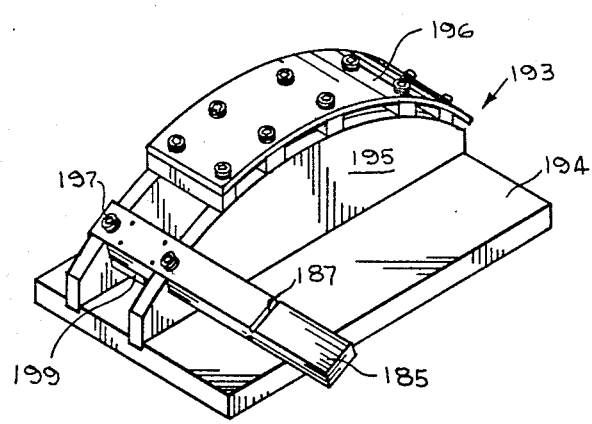
FIG. 12 is a perspective view of a stand and a gate calibration block used in calibrating the gates before any welds are tested.

The positioning of the calibration blocks with respect to the transducers is accomplished with calibration stand 193 shown in FIG. 12. This stand includes a base 194 and two upright supports 195 on which is mounted a band 196. This band should be of the same width and thickness as the band which is mounted on the pipeline P, so that the carriage may be placed on either band. Supports 195 have recesses into which the ends of the calibration blocks may be placed and retained by bolts 197 extending through holes 198 in the blocks. Locator pads 199 are attached to the ends of the calibration blocks in order to facilitate the proper positioning of the blocks on the stand 193.

To calibrate the transducers and the gates, the carriage is mounted on the band 196. The carriage-mounted components of the subsystem are mounted on the carriage and the calibrating steps described above are performed, with the calibrating blocks being mounted on the stand as required.

As is illustrated in FIGS. 2, 3 and 4, a watertight box indicated generally at 280 is mounted on side frame plate 80 by means of a stanchion 281 extending from plate 80 and screws 282 joining stanchion 281 and box 280. Box 280 holds electrical connections 285 for facilitating the transmission of electrical signals between the test head 30, odometer 40, flaw detector 50, multiplex switch 55 and signal processor 60. These electrical connections 285 include electrical sockets and electrical plugs indicated generally at 286 and wires indicated schematically at 287. In addition, box 280 holds multiplex switch 55.

As is shown in FIGS. 2 and 4, a bracket 290 is mounted by suitable means such as welding to the rear end of side frame plate 80 at right angles to said plate 80 and is supported in part by gusset 291. The outer end of bracket 290 carries the pressure regulating device, indicated generally at 35, and attached to bracket 290 by screws 292. Conduits 36, 37, 38, which preferably are made of rubber hose, connect the coupling liquid source 31 (not shown in FIGS. 2, 3 and 4), the pressure regulating device 35 and the test head 30 as described above. A pet cock 293 enables the operator to shut off the flow of coupling liquid to device 35 when desired.

FIGS. 13 and 14 illustrate the details of the pressure regulating device 35. FIG. 13 shows the device 35 in its open position; FIG. 14 shows the device 35 in its closed position. Device 35 comprises a body which, for ease of construction, is formed of three sections 320, 321 and 322 which are joined together by appropriate means such as bolts 323. The body has a generally cylindrical hollow cavity or interior 324. A cylindrical spool 325, which may be referred to as a valve member, is disposed slidably in said cavity 324. As may be seen from FIGS. 13 and 14, this spool is somewhat shorter than the cavity 324 so that the spool 325 may slide back and forth in cavity 324. A bolt 326 extends from outside section 320 through a hole in section 320 and into cavity 324. The inner end of the bolt 326 engages a spring 327 which is disposed in spool 325 and presses spool 325 away from bolt 326 towards section 322. For the purpose of engaging the spring, the inner end of bolt 326 has an annular shoulder 328; bolt 326 may be screwed or unscrewed into cavity 324 to change the compression of spring 327 and the force which spring 327 exerts on spool 325.

Section 321 of device 35 has first and second channels 329 and 330 which are coaxially aligned on opposite sides of section 321 and which communicate between the cavity 324 and the exterior of device 35. A third channel 331 extending through section 322 communicates between cavity 324 and the exterior of device 35. Conduit 36, described above, which may be referred to as first flow means communicates between first channel 329 and the source of coupling liquid 31. Conduit 37, which may be referred to as second flow means, communicates between second channel 330 and the hollow chamber 126 in the test head 30. Conduit 38 which may be referred to as third flow means, communicates between hollow chamber 126 of test head 30 and third channel 331.

Spool 325 has an exterior annular groove 332 about its midsection. When the groove 332 is aligned with channels 329 and 330 as in FIG. 13, coupling liquid may flow from said source 31 through conduit 36, channel 329, groove 332, channel 330 and conduit 37 to test head 30. When groove 332 is not aligned with channels 329 and 330, as in FIG. 14, the flow of coupling liquid from the source 31 to test head 30 is cut off.

For the purpose of exerting a force on spool 325 in opposition to the force of spring 327, a piston indicated generally at 340 is secured by screw 341 to the end of spool 325 away from bolt 326. This piston is formed of a circular disc 342, an annular flexible membrane 343, annular disc 344 and screws 345. As is shown, membrane 343 is held between sections 321 and 322 and between discs 342 and 344 which are joined by screws 345. Piston 340 seals off flow from conduit 38 to spool 325. The dimensions of the parts are such that when spool 325 is pressed against wall 346 of section 322 by spring 327, groove 332 is aligned with channels 329 and 330. When spool 325 is in such position, a small amount of air, coupling liquid and other matter may flow through conduit 38, hole 347 in coupler 348 and recess 349 in section 322, which is provided for that purpose, and out exhaust channel 350. When the pressure of the flow from channel 38 acting on piston 340 is sufficient to overcome the force of spring 327 and other forces acting on spool 325, the piston 340 and spool 325 will move toward nut 326 and the flow of coupling liquid through channel 37 to test head 30 will be stopped. See FIG. 14.

The force of spring 327 on spool 325 may be controlled by turning nut 326, as described above. In this way, the preselected pressure of coupling fluid in chamber 126 can be adjusted within limits. Thus, the nut 326 can be referred to as means for adjusting the magnitude of the preselected pressure. As explained above, conduit 38 communicates with chamber 126 and thus the pressure of the liquid in chamber 126 will be about the same magnitude as the pressure in conduit 38. When this pressure is greater than the preselected pressure determined by the selection of spring 327, the adjustment of bolt 226 and other factors, the spool 325 will prevent the flow of coupling liquid to chamber 126. As soon as the pressure in chamber 126 and conduit 38 falls below the preselected pressure, the spring 327 will move spool 325 to realign channels 329 and 330 with groove 332 and coupling liquid will flow to chamber 126 until the coupling liquid in chamber 126 regains the preselected pressure.

Ports 351 in section 321 permit the discharge of small amounts of liquid from cavity 324.

Although in the preferred embodiment pressure regulating device 35 is shown to include spool 325 which is responsive to the forces of spring 327 and piston 340 in order to control the flow of coupling fluid, obviously many other devices to control the flow of coupling fluid would fall within the scope of this invention. For example, an electric switch responsive to piston 340 could control an electro-mechanical device which opens and shuts conduit 36 and thus maintains the pressure in chamber 126 at a preselected magnitude. Alternatively, such a switch responsive to piston 340 could control the operation of pump 32 and thereby control the pressure in chamber 126.

The odometer wheel 355 is trunnion mounted in a bracket indicated generally at 356. This wheel 355, as is seen best in FIG. 2, has a rim 357 which engages pipeline P. Preferably this rim 357 is made of rubber or some other substance which will not slip on pipeline P. Bracket 356 comprises arms 358 and 359 and bridge 360, which are joined together by screws 361 as seen in FIG. 15.

Bracket 356 is mounted to side frame plate 80 by means of bolts 362 and 363 and block 364. Bolt 363 extends through a hole in the forward end of arm 358 and into block 364 so that arm 358 may pivot about bolt 363. A spring 365, mounted around a base projecting from block 364, presses arm 358 so that rim 357 is continually pushed into engagement with the pipeline P.

Figure 16:
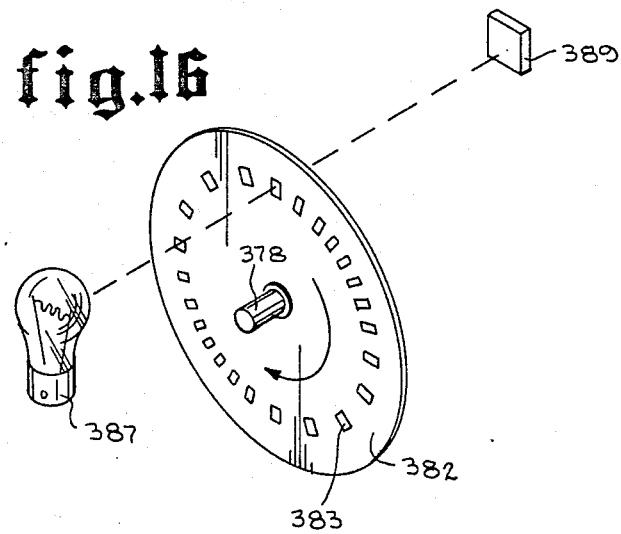
FIG. 16 is a schematic illustration of the photographic disc used in the odometer.

A watertight cannister 370 is mounted on arm 358 between arm 358 and side frame plate 80 by suitable means such as screws. This cannister 370 is formed of a cylindrical wall 371, an end plate 372, a base 373 and a block 374, which are joined together by suitable means such as screws. Cannister 370 contains a shaft encoder which measures the revolutions of wheel 355 and will now be described. Wheel 355 is mounted on rotating shaft 375 which is carried by ball bearings 377. Shaft 375 has an end 378 of diminished diameter and projects through a hole in base 373 into a cavity 379 between base 373 and block 374. Two discs 380 and 381 are mounted on the end 378 of shaft 375 and retain between them a disc of photographic film 382. This film 382, illustrated schematically in FIG. 16, is generally opaque, but has evenly spaced translucent windows 383 around its rim. These windows 383 revolve with shaft 375 in a gap between base 373 and block 374 and pass through channel 384 in base 373 and block 374. This channel 384 communicates between chamber 385 in base 373 and chamber 386 in block 374. Chamber 385 contains a lamp 387 which receives current from wire 388 running through a channel in base 373 and block 374, as shown in FIG. 15. Chamber 386 contains a photocell 389 which is sensitive to light and generates electric pulses when it receives light. These pulses are transmitted by wire 390 to a circuit-board 391 mounted on block 374 by unnumbered screws. Circuit-board 391 amplifies these pulses from photocell 389 and transmits them to the signal processor 60 via cable 71g which passes through a hole in cylindrical wall 371. Thus, as the shaft 375 turns, the windows 383 permit flashes of light from lamp 387 to impinge on photocell 389. The frequency of these flashes of light is directly proportional to the speed of revolution of shaft 375 and wheel 355 and therefore is a measure of the distance traveled around pipeline P by the test head 30. A translucent plastic plug 392 filling a hole in arm 358 glows when lamp 387 is on and thus provides the operator with an easy way to determine whether lamp 387 is functioning. As described above signals from the photocell 389 are transmitted to the signal processor 60 via cable 71g and from there to the chart recorder 70 via cable 71f.

The side frame plate 80, carrying the test head 30, the pressure regulating device 35, the odometer 40, the multiplex switch 55 and other components of the apparatus is carried around the pipeline P by means of a track 393 and carriage indicated generally at C. Side frame plate 80 is attached to carriage C by means of retaining bolts R. Such tracks and carriages are old in the art and do not constitute part of this invention except in combination with the ultrasonic inspection apparatus. The preferred track and carriage are illustrated in U.S. Pat. 3,604,612 (1971) to Miller and Nelson. However, the inspection subsystem of this invention may be used with any other suitable means for moving the transducers to traverse the weld under inspection.

Track 393 is mounted circumferentially around the pipeline P adjacent the weld W and includes a flexible band B elevated from the pipeline P by pins 394. Three idle rollers 395 and a drive roller 396 engage the rims of band B in order to retain the carriage C on band B and drive it around band B. A toggle mechanism controlled by handles 397 permits the moving apart of the rollers and the removal of the carriage C from the band. The drive roller 396 is driven by an electric motor 398 which may be turned on and off by switch 399.

Preferably the track and carriage also are suitable for carrying a welding device, so that the same or similar track and carriage may be used to form and inspect the weld. If this method is used, the proper alignment of the test head with respect to the weld is greatly facilitated because the track and carriage had to be properly aligned to form the weld and in part the configuration and alignment of the track and carriage determined the shape and alignment of the weld. If possible, it is desirable to inspect the weld after it is formed and before the track is moved, so that the track already will be properly aligned with respect to the weld. This technique may be accomplished by removing the weld device from the carriage after the weld is formed, attaching the appropriate components of the inspection subsystem to the carriage and performing the inspection. Alternatively, two separate carriages may be used. Clearly the technique greatly improves the ease and rapidity with which the inspection may be performed. Of course the alignment of the test head with respect to the weld is important in order to receive meaningful signals from the transducers. Further, if the test head lifts off of the pipeline P, the coupling fluid will no longer be maintained between the transducers and the pipeline and the waves wtill not propagate between the pipeline annd the transducers.

The electronic circuitry associated with the signal processor 60 is illustrated schematically in FIG. 17. A timing chart whcih further illustrates the operation of the components in FIG. 17 appears in FIG. 18.

As previously noted, the flaw detector 50 used in the aparatus described herein is well known to those skilled in the art. The specific flaw detector used in the preferred embodiment of the invention herein contains a mechanism for generating synchronization pulses at periodic intervals. This synchronization pulse 400 is represented on line J in FIG. 18 with specific pulses occurring at times T0 and T5 on TIME line N. The synchronization pulses from the flaw detector 50 are received by the signal processor on line 401 which forms and input to delay means 402 and ring counter 404. The delay means 402, a device whose structure and operation are known to those skilled in the art, serves the function of delaying the input pulse for a preselected time before outputting the pulse on line 406. The pulse on line 406 returns to the flaw detector in which it is used to generate excitation pulses 408 which are shown on line K at times T1 and T6 in FIG. 18 to occur at a delay time T1 minus T0 after the synchronization pulse on line J is emitted by the flaw detector. This delay in time between the time that the synchronization pulses is emitted on line 401 at time T0 and the time when the excitation pulse is emitted at time T1 is necessary in order to allow the circuitry in FIG. 17 sufficient time to function as hereinafter described.

The synchronization pulse 400 is input to ring counter 404 which outputs the pulse on one of the four lines 410, 412, 414, and 416. The ring counter 404 is a device whose operation and structure are known to those skilled in the art. The ring counter 404 receives an input pulse on line 401 and outputs this pulse on only one of the four lines 410, 412, 414 and 416. The ring counter 404 generates output pulses sequentially on lines 410, 412, 414, and 416, but only generates one ouput pulse for each input pulse. For example, on the first input pulse on line 401 the counter 404 issues a pulse on line 410; on the second input pulse on line 401, the counter 404 issues a pulse on line 412, etc. After the counter issues an output pulse on line 416, the sequential output continues with the next output pulse occurring on line 410.

Pulses on lines 410, 412, 414, and 416 which serve as control pulses for transducers 1, 2, 3, and 4, respectively, are input to multiplex switch 55, gain adjustment network 420, channel selector switch 422, and gates 423, 425, 427 and 429.

The gain adjustment network 420 is a device whose structure and operation are known to those skilled in the art. The gain adjustment network 420 outputs onto line 424 a voltage of constant amplitude whereby this amplitude can be preset to different magnitudes depending on which of lines 410, 412, 414 and 416 a pulse is received. This adjustment of gain is necessary because different transducers receiving a wave with the same amplitude will convert the wave with varying amplitudes due to nonuniformity of operating characteristics of the transducers. The signal on line 424 is used by a gain control device on the flaw detector 50 to multiply the signal converted by each transducer by an appropriate factor to eliminate the effects of the varying operating characteristics of transducers.

The channel selector switch 422 is manually preset to connect electronically one of the four lines 410, 412, 414 and 416 to line 426. The pulse on line 426 is lengthened by pulse stretcher 428, whose operation and structure are known to those skilled in the art, which applies its ouput to line 430. Line 430 controls the Z-modulation on the oscilloscope screen located on the flaw detector 50. The Z-modulation signal functions to display a trace on the oscilloscope screen when the logic state on line 430 is high and deletes the trace when the logic state on line 430 is low. Thus the switch 422 is used to select the particular transducer whose performance is to be viewed on the oscilloscope screen.

Lines 410, 412, 414 and 416 extend via cable 71d from the ring counter 404 to a multiplex switch 55 which is physically located within the watertight box 280. Switch 55 is a device whose operation and structure are known to those skilled in the art which serves to connect electrically line 71a to one of the transducers 130-133 on lines 434, 436, 438 and 440. Switch 55 conects line 71a to line 434 responsive to a pulse on line 416, to line 436 responsive to a pulse on line 414, to line 438 responsive to a pulse on line 412, and to line 440 responsive to a pulse on line 410.

Pulses on lines 410, 412, 414, and 416 serve as inputs to gates 423, 425, 427 and 429, respectively, whereby said gates serve the function of selecting only those reflected waves received by the transducers during specified time periods which correspond to reflections from within the region of the test object to be inspected.

As illustrated in FIG. 17, gates 429, 427, 425 and 423 operate on signals corresponding to those received by transducers 130–133 on lines 434, 436, 438 and 440, respectively. Although only gate 429 is illustrated schematically in FIG. 17, it is to be understood that gate 429 is identical in operation and structure to gates 423, 425 and 427.

Figure 18:
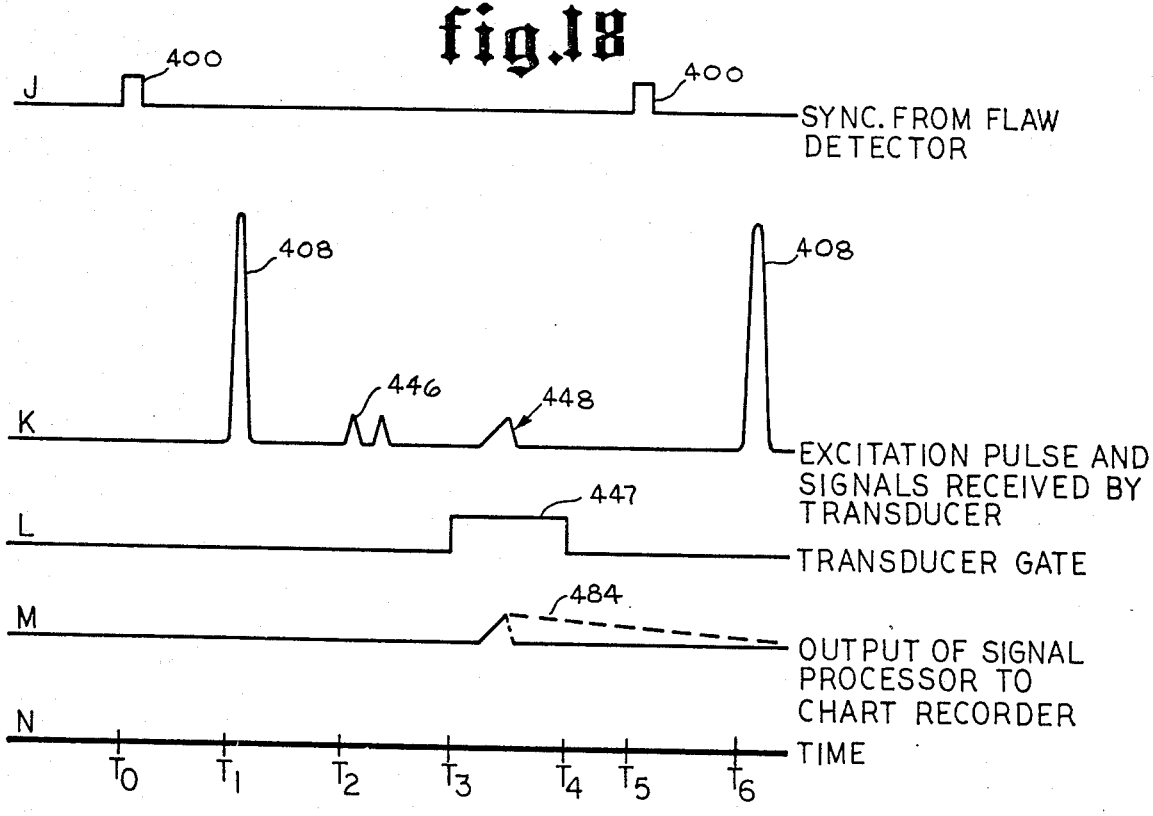
FIG. 18 is a schematic illustration of the signal-time relationships of the signal processor.

Line K of FIG. 18 illustrates the usual reflection pattern using the invention as described herein when an excitation pulse 408 is emitted from a transducer. Considering the excitation pulse 408 generated at time T1, the wave emitted from the transducer is reflected from the surface of the test object, and the reflected wave 446 is propagated back to the transducer and received at time T2. This reflection from the surface of the test object does not render any useful information regarding flaws, and therefore, it is desirable not to display, record, or otherwise monitor this reflection for purposes of analysis for flaws. Also, it is desirable not to display, record, or otherwise monitor any wave reflections reaching the transducers except those that are known to have originated in a region of the test object where flaws, if any, will occur. As illustrated in lines K and L of FIG. 18, when it is known that a reflected wave such as wave 448 which is reflected from the region of interest must reach the transducer between time T3 and T4, then only signals received by the transducer between times T3 and T4 need be analyzed for the purpose of detecting the presence of flaws. Thus, it is desirable to produce a gate 447, as shown in FIG. 18, which allows the signal processor to output signals representing only reflections from the region to be inspected so that only a signal caused by reflection 448 is recorded for flaw analysis.

There are two methods for determining the position of the gate 447 as shown on line L in FIG. 18. Firstly, the gate can be triggered to occur at a specified time after the occurrence of the excitation pulse 408. However, this method has the disadvantage that the timing of gate position relative to the time interval in which the waves are reflected from the region of interest is very sensitive to slight position changes of the transducers. The sensitivity of the gate is reduced and therefore the performance improved by triggering the gate 447 responsive to the wave 446 which is reflected from the surface of the test object rather than responsive to the excitation pulse 408. Since the thickness of the pipe is a constant, any repositioning of the transducer, even if moved a significant distance closer or farther from the pipe surface, will have only a slight effect on the time in which reflections from the region of interest reach the transducer, with respect to the time at which the reflection from the surface of the test object reaches the transducer, since the distance which the wave travels through the pipe will likely vary only slightly. The method of triggering the gate from the wave reflected from the surface of the test object is implemented in the gate network illustrated in FIG. 17. This method is known as interface triggering and is well known in the prior art.

As shown in FIG. 17, a synchronization pulse originating from the flaw detector on line 401 is received by window delay unit 450 via line 416. The window delay unit 450, which is identical in operation and structure to gate delay unit 454, is a component whose operation and structure are known to those skilled in the art whose function is to delay a pulse received on line 416 at time T0 by a preselected time interval before outputting the pulse on line 458. The pulse on line 458 is input to window generator 452 which is a pulse stretcher whose setting determines the length of the output pulse therefrom. The time delay on window delay unit 450 is preselected to a delay approximately equal to the time interval T2 minus T0 since it is known that the wave emitted by a transducer will have returned from the surface of the test object at time T2 and that no reflections before time T2 are of interest in triggering gates. However, since it is desired to trigger a gate as previously discussed relative to the wave 446 which is reflected from the surface of the test object, the window generator 452 is preset to a time interval in which it is known that the reflection 446 will reach the transducer.

All signals on the flaw detector screen, such as those on line K in FIG. 18, are transmitted to a nonlinear amplifier 462 of the signal processor via line 460. The amplifier 462 is a device whose structure and operation are known to those skilled in the art which amplifies signals with amplitudes greater than a preselected threshold to a specified saturation amplitude and outputs these signals to trigger 464 via line 466. The thershold level of amplifier 462 is preferably preset to a level in a region above the amplitude of spurious signals received by the transducer but below the amplitude of the wave 446 which is reflected from the surface of the test object such that wave 446 causes an output of the amplifier 462 to trigger 464. Trigger 464, whose operation and structure are known to those skilled in the art, performs the logic function AND on input signals from amplifier 462 via line 466 and from window generator 452 via line 468. Thus, trigger 464 outputs a logic high signal only when both of its inputs from amplifier 462 and window generator 452 are at the appropriate logic high state. Thus, since window generator 452 functions to ouput a high signal during the time interval in which the wave 446 is expected to be received by the transducers, then trigger 464 will output a logic high signal at time T2 when the amplifier 462 generates a logic high output responsive to wave 446. Thus, trigger 464 serves the function of generating an output signal when the wave 446 is detected by the transducer.

The time interval between the time when the wave 446 which is reflected from the surface of the test object is received by the transducer and the time when waves which are reflected from the region to be inspected are received is determined by calibration techniques which have been described in accordance with the illustration of FIG. 7. One time interval which is set during calibration is the time interval which extends from the beginning of the wave 446 which is reflected from the surface of the test object at T2 to the beginning of the gate 447 at T3. The beginning of the gate 447 at T3 becomes the near boundary. Thus, the gate 447 excludes or eliminates all of the waves between times T2 and T3 that are received by the transducer since they are reflected from an area between the surface of the test object and the near boundary of the region of interest, and thus are of no interest in the analysis of the weld for flaws.

The gate generator 456 is a pulse stretcher whose operation and structure are known to those skilled in the art which receives a pulse via line 472 from gate delay unit 454 at time T3. The width of transducer gate 447 as shown on line L in FIG. 18, is determined by adjusting the length of the pulse output from the gate generator 456 wherein the pulse length is preset during calibration. By monitoring the gate and the signals representing reflected waves on the oscilloscope screen during the calibration process, the operator sets the end of the gate 447 to coincide with the signal caused by a wave reflected by the appropriate reflective surface of a notch on a gate calibration block. The end of the gate 447 at time T4 thus determines the far boundary of the region of interest to be inspected. The output of the gate generator 456 via line 476 closes the electronic switch 474, a device whose operation and structure are known in the art, which allows the signal from the screen of the flaw detector 50 to be input to peak voltage detector unit 478 via line 480. Since the gate generator 456 closes the switch 474 only during the interval between T3 and T4 as shown on line L in FIG. 18, the only signals which are input to peak voltage detector 478 (See line M) are those which occur between times T3 and T4. These signals which appear on the input 480 of peak voltage detector 478 are thus representative of waves which are reflected between the near and far boundaries of the region of the test object to be inspected and received by the transducer. The peak voltage detector 478, a device whose operation and structure are known to those skilled in the art, stores the highest peak of its input signal and allows the peak slowly to decay in amplitude as the signal is ouput to the chart recorder on line 486 via cable 71f. The output of the peak detector 478 is illustrated as wave 484 on line M of FIG. 18.

For calibration of each gate 423, 425, 427 and 429, a switch 488 is provided to connect a line 490 which is the input to the gate display of the screen of the flaw detector to the output of the window generator 452 via line 468 or to the output of the gate generator 456 via line 476. The switch is positioned such that window generator output 468 is input to the flaw detector screen via line 490 when it is desired to adjust window delay 450 and window generator 452 for defining the trigger window which uses wave 446 as a trigger for the gate 447. When the gate 447 is calibrated, the switch 488 is positioned to connect the output of gate generator 456 to the screen of the flaw detector via line 490 so that gate delay unit 454 and gate generator 456 may be set properly to define the near and far boundaries of the region of interest.

Signals from the odometer 40 are received by the signal processor 60 on line 71g. These signals indicate the distance which the test head has traveled over the surface of the test object from a known point. These signals on line 71g form a second input to the chart recorder via cable 71f. An accumulator 492 sums the increments of distance traveled and the output of the accumulator may be displayed on an alphanumeric display 496 after the accumulated sum is processed by decoder unit 498.

Figure 19:
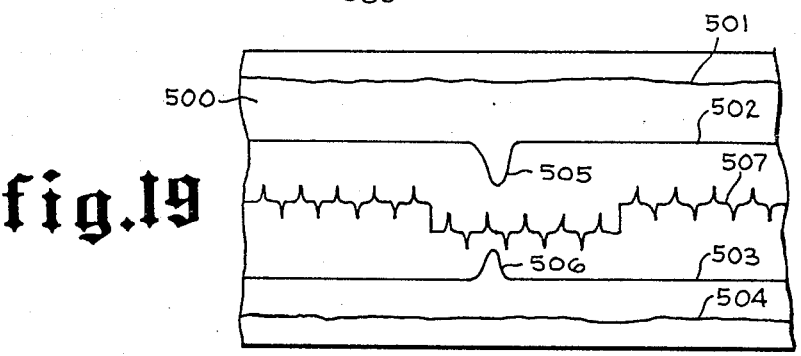
FIG. 19 is a schematic illustration of a strip chart showing signals from the four transducers and the odometer as recorded by the chart recorder.

FIG. 19 is a schematic illustration of a strip chart 500 showing traces 501, 502, 503, and 504 from the four transducers 130, 131, 132 and 133 respectively. Deflections 505 and 506 on traces 502 and 503 indicate a flaw or other discontinuity in the weld. Trace 507 provides a record of the signals from odometer 40 and thus indicates to the operator the location of the flaw with respect to a known reference point on the weld.

In operation, first the side frame plate, carrying the test head, pressure regulating device, odometer and other carriage-mounted components of the insepction subsystem, is mounted on the carriage. The carriage is placed on the calibration strand to calibrate the transducers and gates. The transducer calibration block is mounted on the stand under the test head and the attitude of each transducer is adjusted to direct its waves into the weld as desired. The gate calibration blocks are mounted on the stand under the test head and the gates are set to eliminate signals from the weld reinforcements and other areas not to be inspected. The carriage then is removed from the calibration stand and is placed on the track around the pipeline adjacent the weld. Preferably this track also guided the welding device which made the weld and preferably the track has not been moved since the weld was made. The test head is filled with coupling liquid. The carriage carries the test head around the pipeline over the weld and the transducers transmit ultrasonic waves through the coupling liquid in the test head and into the pipeline. The transducers receive waves which are reflected from flaws in the weld and which propagate through the pipeline and coupling liquid to the transducers. Signals caused by these flaws are transmitted to the flaw detector and the signal processor and are recorded by the chart recorder. The pressure regulating device maintains the coupling liquid in the test head at a constant preselected pressure. This pressure may be adjusted to keep leakage of coupling liquid minimal and yet insure that there is always coupling liquid between the transducers and pipeline while the weld is being inspected or tested. The odometer measures the distance traveled around the pipeline by the carriage and test head and this distance is recorded with flaw signals from the transducers to aid in locating flaws detected by the transducers. When the weld has been inspected, the carriage is removed from the track.

Thus, it can be seen from the foregoing that an invention has been provided which keeps the loss of coupling liquid minimal and yet insures that there is always coupling liquid between the transducers and the pipeline. Further, the invention solves the problem of rapidly and properly aligning the path of the transducers with respect to the weld and the problem of determining the location of detected flaws. Also, this invention solves the problem of eliminating signals associated with the upper and lower reinforcements of the weld.

ALTERNATIVE EMBODIMENTS

Figure 20:
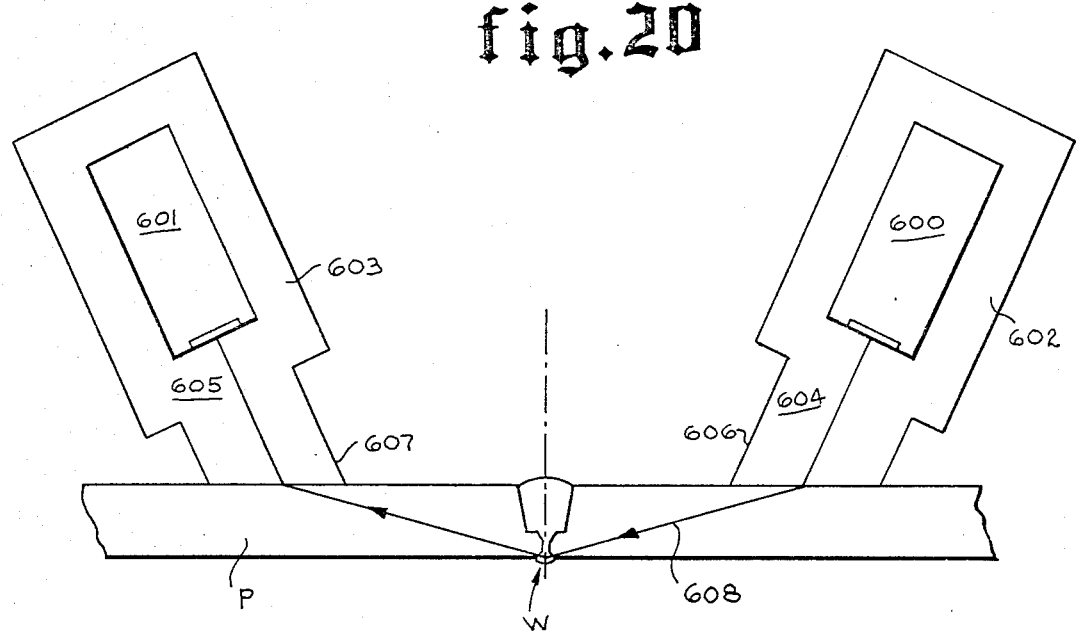
FIG. 20 is a schematic illustration of an alternate embodiment of the invention.

FIG. 20 is a schematic illustration of an alternate embodiment of the invention. From the foregoing, it is obvious that this invention is not limited to transducers enclosed in one housing or to transducers which both transmit and receive ultrasonic waves. FIG. 20 shows a transducer 600 which transmits, but does not receive ultrasonic waves, and a transducer 601 which receives, but does not transmit waves. Inspection with such transducers is well known in the art. Each of these transducers is disposed on opposite sides of weld W to be tested and each is carried in its own housing, numbered 602 and 603 respectively. Each of the housings has a hollow chamber, numbered 604 and 605 respectively, filled with coupling liquid and with an opening toward the surface of pipeline P. Seals 606 and 607 are mounted on housings 602 and 603, respectively, slidably engage the surface of pipeline P and retain coupling liquid between the transducers 600 and 601, respectively, and the surface of pipeline P. One pressure regulating device which functions as pressure regulating device 35 described above may be connected to chamber 604 to keep the coupling liquid in that chamber at a constant preselected pressure. Similarly, another such pressure regulating device may be connected to chamber 605 to keep its pressure at a constant preselected magnitude. Alternatively, the same pressure regulating device which function as device 35 may be connected both to chamber 604 and to chamber 605. The housings 602 and 603 may be carried by track 393 and carriage C around the circumference of pipeline P and inspect weld W. A flaw is indicated by a distortion of the wave 608 propagating between transducer 600 and transducer 601. The odometer 40 may measure the distance traveled by the transducers around pipeline P.

The foregoing disclosure and description of the invention are illustrative and explanatory thereof, and various changes in the size, shape and materials, as well as in the details of the illustrated construction may be made within the scope of the appended claims without deprting from the spirit of the invention. Clearly the invention is useful for inspecting not only tubular test objects such as pipelines, but also test objects of many other sizes and shaped, such as test objects with planar surfaces. Further, clearly the invention is useful in testing test objects other than welds, such as sheets of metal without welds. In addition, clearly many aspects of this invention are not limited to the use of ultrasonic transducers, but could include other means for detecting flaws in the test object.

What is claimed is:

1. An ultrasonic apparatus for detecting flaws in a test object having at least one surface, said apparatus being adapted to receive coupling liquid for transmitting ultrasonic waves between said apparatus and said test object, said apparatus comprising:

a source of said coupling liquid;
a housing having a hollow chamber with an opening towards the surface of the test object;
a seal attached to the housing around the opening, said seal slidably engaging the surface of the test object and retaining said coupling liquid in the hollow chamber of said housing;
a pressure regulating device in communication with said hollow chamber and with said source for supplying said coupling liquid to the chamber from said source and for maintaining said liquid at substantially constant pressure within the chamber;
at least one ultrasonic transducer mounted in said hollow chamber so that said coupling liquid in said housing conducts ultrasonic waves between said transducer and said test object;
mens cooperating with said housing for moving said housing so as to cause the transducer to traverse the surface of the test object in such proximity to the test object that ultrasonic waves may propagate through the coupling liquid and between the transducer and the test object;

said pressure regulating device including means for stopping the flow of said coupling liquid from said source to said chamber when the coupling liquid pressure within the chamber reaches a preselected magnitude and for permitting said flow when said pressure becomes less than said preselected magnitude;

said pressure regulating device having a hollow cavity and first, second and third channels communicating between said cavity and the exterior of said device;

first flow means communicating between said source of said coupling liquid and said first channel;

second flow means communicating between said second channel and said hollow chamber;

third flow means communicating between said hollow chamber and said third channel;

a valve member disposed in said cavity of said pressure regulating device, said valve member being responsive to pressure of said liquid in said third channel so that said valve member stops the flow of said coupling liquid through said cavity when said pressure in said third channel reaches a preselected magnitude and permits the flow of said coupling liquid through said cavity when said pressure in said third channel reaches said preselected magnitude, whereby said coupling liquid flows from said source through said first flow means, said first channel, said cavity, said second channel and said second flow means to said hollow chamber and from said hollow chamber through said third flow means and third channel to said cavity except when the pressure in said hollow chamber, third flow means and third channel reaches a preselected magnitude and said valve member stops the flow of said coupling liquid through said cavity to said hollow chamber, thus maintaining substantially constant liquid pressure within said chamber.

2. The apparatus of claim 1 wherein the valve member maintains the pressure of said coupling liquid within the housing at a magnitude such that leakage of said coupling liquid past the seal is minimal and said coupling liquid is maintained continually between said transducer and said test object.

* * * * *